United States Patent [19]

Traish et al.

[11] Patent Number: 5,439,796
[45] Date of Patent: Aug. 8, 1995

[54] SPECIFIC MONOCLONAL ANTIBODIES AGAINST A DEFINED EPITOPE OF PROGESTERONE RECEPTOR AND METHODS FOR THEIR USE

[75] Inventors: Adbulmaged M. Traish, Belmont; Herbert H. Wotiz, Milton, both of Mass.

[73] Assignee: Trustees of Boston University, Boston, Mass.

[21] Appl. No.: 77,902

[22] Filed: Jul. 23, 1993

Related U.S. Application Data

[63] Continuation of Ser. No. 762,246, Sep. 19, 1991, Pat. No. 5,283,190, which is a continuation of Ser. No. 494,356, Mar. 16, 1990, abandoned, which is a continuation-in-part of Ser. No. 388,091, Jul. 31, 1989, abandoned.

[51] Int. Cl.$^6$ .................. C12Q 1/00; G01N 33/53; A61K 35/14; C07K 3/00
[52] U.S. Cl. .................. 435/7.1; 435/7.2; 435/810; 530/388.22
[58] Field of Search ............ 435/7.1, 7.2, 810; 530/388.22

*Primary Examiner*—Robert A. Wax
*Assistant Examiner*—Hyosuk Kim
*Attorney, Agent, or Firm*—David Prashker

[57] ABSTRACT

The present invention provides unique prepared immunogens, site-specific monoclonal antibodies against an epitope of progesterone receptor protein, and an immunoassay to determine the functional integrity of the progesterone receptors in a cellular sample. Collectively or individually the component parts of the invention provide the ability not only to identify accurately the presence of progesterone receptor but also the capability of determining whether the progesterone receptor exists in a clinically normal or abnormal state.

4 Claims, 8 Drawing Sheets

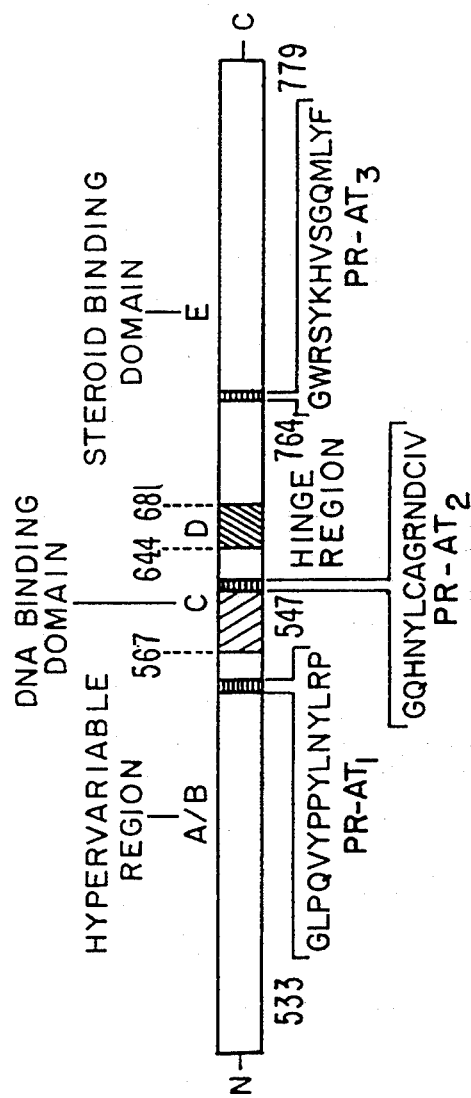

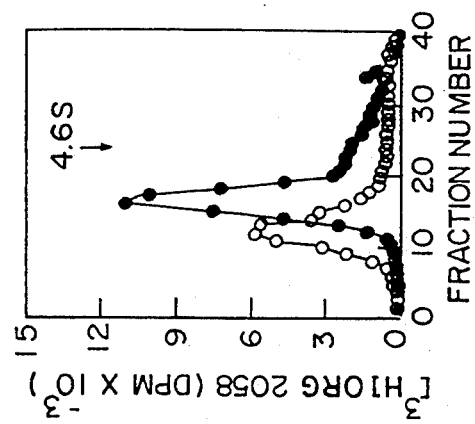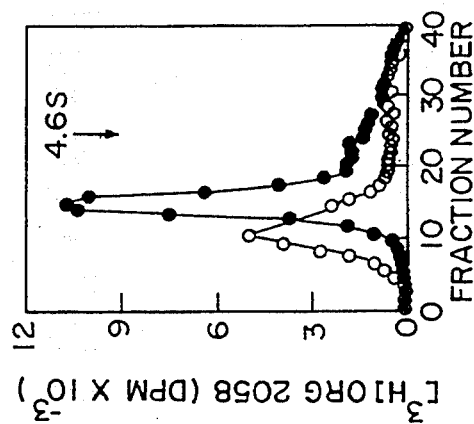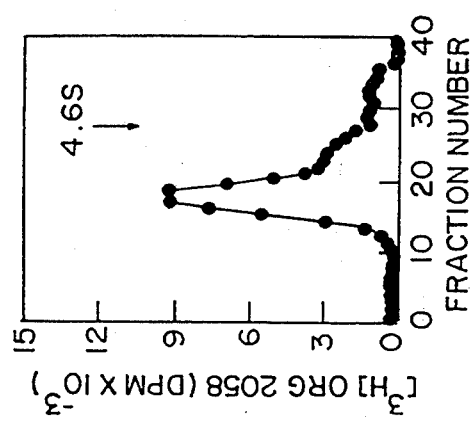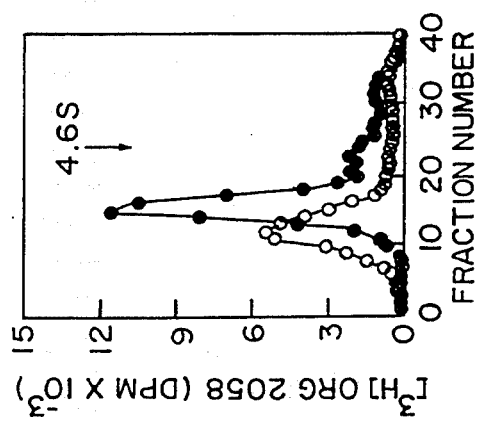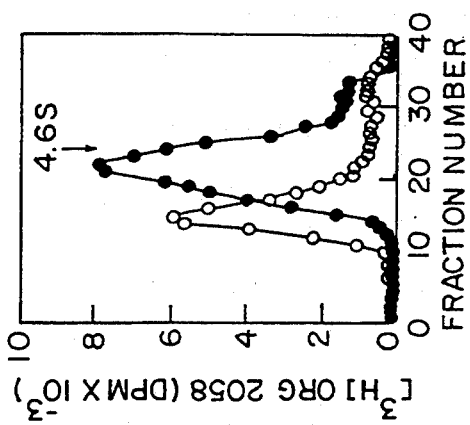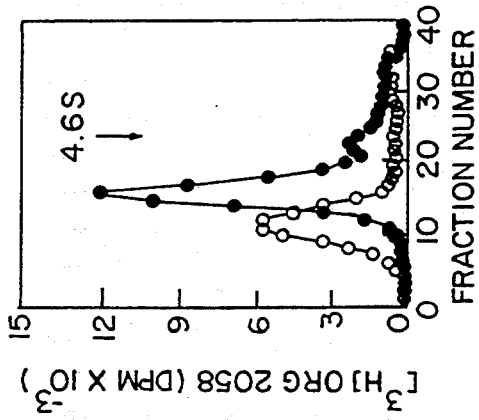

SPECIFIC MONOCLONAL ANTIBODIES AGAINST A DEFINED EPITOPE OF PROGESTERONE RECEPTOR AND METHODS FOR THEIR USE

CROSS-REFERENCE

This is a continuation of application Ser. No. 07/762,246, filed Sep. 19, 1991, now U.S. Pat. No. 5,283,190, which was a continuation of application Ser. No. 07/494,356, filed Mar. 16, 1990, abandoned, which was a continuation-in-part of application Ser. No. 07/388,091, filed Jul. 31, 1989, abandoned.

RESEARCH SUPPORT

The research for the present invention was supported by the Boston University Community Technology Foundation and the Hubert H. Humphrey Cancer Research Center.

FIELD OF THE INVENTION

The present invention is concerned with the development of site-specific monoclonal antibodies raised against preselected functional domains within progesterone receptor protein; and is particularly directed to the use of an epitope-specific monoclonal antibody directed against a single domain of human progesterone receptor as a means for evaluating the intracellular functionality of progesterone receptors.

BACKGROUND OF THE INVENTION

Progestins are a class of naturally occurring steroidal hormones which are produced in the ovaries and other tissues in the body and which directly influence the growth and function of specific target tissues in humans and animals. Although a variety of naturally occurring and chemically synthesized progestins have been identified and characterized (including 17a-hydroxyprogesterone, norethisterone acetate, medroxyprogesterone, and megestrol acetate), perhaps the best known is progesterone [Pregn-4-ene-3,20-dione] which is endogenously secreted during the latter half of the menstrual cycle.

progestins mediate their action by binding to an intracellular protein, presumably a nuclear protein, identified as "progesterone receptor" and also abbreviated as "PR". The presence of this intracellular PR provides and accounts for new protein synthesis by progesterone dependent cells. The progesterone receptor in the absence of the progesterone hormone is biologically inactive both in vivo and in vitro; and, if the cells or tissues are homogenized and fractionated into cytosol and nuclear fractions, the progesterone receptor is found as a soluble protein in the cytosol. Although the precise molecular mechanism of progesterone action remains poorly understood, the generally accepted sequence of events is believed to be as follows: When progesterone is introduced to the target cells and tissues, there is specific binding of progesterone to PR protein which results in the formation of a progesterone/receptor protein complex. Also, at a time subsequent to progesterone binding, a process termed activation and/or transformation ensues which leads to the formation of functional progesterone/receptor complexes having a high affinity for the nuclear components, the DNA, of the target cell. Once the hormone/receptor protein complex is physically formed, it is said to translocate as a complex into the nucleus of the cell where it binds to specific DNA sequences known as progesterone responsive elements on the chromosomes and initiates messenger ribonucleic acid (mRNA) transcription. New messenger RNA is then synthesized, chemically modified, and exported from the nucleus into the cytoplasm of the cell where ribosomes translate the mRNA into new proteins. This is the well-recognized progesterone effect on the cell—that is, the initiation of new protein synthesis.

The theoretical premise and the generally accepted, though poorly understood, mechanism of action regarding progesterone hormones, progesterone receptor proteins, and their interactions are described in greater detail by the following publications—all of Which are merely representative of the ongoing investigations in this field. These are: Horowitz et al., *Recent Progress In Hormonal Research* 41:249-316 (1985) and the references cited therein; Gronemeyer et al., *EMBO J.* 6:3985-3994 (1987); Traish et al., *Endocrinology* 118:1327-1333 (1986); Traish et al, *Steroids* 47:157-173 (1986); Loosfelt et al , *Proc. Soc. Natl. Acad. Sci. USA* 83:9045-9049 (1986); and Misrahi et al., *Biochem. Biophys. Res. Comm.* 143:740-748 (1987); Beato, M., *Cell* 56:335-344 (1989); Evans, R. M., *Science* 240:889-895 (1989); Conneely et al., *Science* 233:767-770 (1986); NaKao, M. and V. K. Moudsit, *B.B.R.C.* 164:295-303 (1989).

In order to truly appreciate the background of the present invention, it is useful to summarize in depth the major details and sequential events presently believed to occur regarding the intracellular protein referred to as "progesterone receptor." In the unbound state, and in the absence of progesterone hormone, the progesterone receptor protein thought to be located in vitro within the cytosol; however some new evidence suggests that the receptor may be located in the nucleus of the cell. The intact PR protein is composed of 933 amino acids. The native human PR proteins found in soluble tissue extract exist as large molecular weight complexes (250,000-300,000 Da). The physico-chemical properties of these receptor proteins, isolated from various human and non-human sources, have been the subject of intensive investigations. It has been demonstrated that PR complex is almost always composed of two proteins termed A and B subunits with molecular weights of 84 and 110 kDa, respectively. In the untransformed state it is thought that these complexes are associated with heat-shock proteins. The biological significance of these large untransformed complexes in vitro remains as yet unclear.

In cell free systems, the solubilized protein prepared in low salt buffers containing both sodium molybdate and proteolysis inhibitors, the progesterone receptor remains untransformed. The human PR protein can be found in alternative molecular forms which sediment at either 8-10S or 4S as determined by sucrose density gradient analysis. The 8S form of PR is believed to be the unactivated, untransformed polymeric form of the PR protein associated with the unbound, native state of receptor in the absence of progesterone. The 8S PR form is a large molecular weight complex, presumably associated with heatshock proteins, that does not bind to nuclei or DNA in vitro and is stabilized as a macromolecule by sodium molybdate.

In comparison, the 4S PR protein form is a monomer—i.e., the protein molecule that can be generated from the 8S form in vitro by treatment with high ionic strength buffers, by elevated temperatures (25°–30° C.), or by increasing salt concentrations (KCl or NaCl). The 4S PR form functionally binds to both nuclei and DNA-cellulose in vitro; it is generally termed the "activated and/or transformed" progesterone receptor protein. From the published reports, it appears that the dissociation of the 8S PR form into the 4S PR form initiates a major structural change in the stereochemical conformation of the protein or by directly exposing the previously hidden DNA binding domain of the receptor molecule.

It is essential also to recognize that progesterone receptor proteins from human and animal sources have been investigated and evaluated in terms of functional domains which provide and are responsible for its characteristic biological and physiological properties. Complimentary DNA (cDNA) of human progesterone receptor has been cloned which, in turn, has led directly to the elucidation of the human ER protein primary sequence. Subsequent studies have further defined the various functional domains of human PR protein as having at least three distinctly different regions, each of which comprises at least one domain and provides unique functional properties and characteristics. See for example Beato, M., *Cell* 5:335–344 (1989).

FIG. 1 illustrates the various domains within the PR protein. The amino-terminal "A/B" region is the hypervariable region and is thought to contribute to full functional activity of the receptor. The middle cysteine rich "C" domain is a critical region for biological activity because it is the DNA-binding region required for interaction with progesterone responsive elements ("PRE"). The "D" region is the hinge region; its function is not yet clear. Region "E" is the carboxy-terminal region and is believed to serve as the progesterone binding domain. The "E" region comprises an amino acid sequence which is generally shared not only among various human and non-human sources of PR; but also is conserved among all the different steroid receptor members throughout the different classes—thereby indicating that substantially similar carboxy-terminal "E" domains are critical for receptors generally throughout all the steroid receptors as a family. Specific publications describing these functional domain investigations, data, and conclusions in greater detail are represented by the following: Green et al., *Nature* 328:134–139 (1986); Hollenberg et al., *Nature* 318:635–641 (1985); Arriza et al., *Science* 237:268–275 (1987); Mishraki et al., *Biochem. Biophys. Res. Comm.* 143:740–748 (1987); Lubahn et al., *Science* 240:327–330 (1988); Chang et al., *Science* 240:324–326 (1988); and Beato, M., *Cell* 56:335–344 (1989).

Overall, it will be noted and appreciated that many investigations of PR protein and the characterization of hormone/PR complexes typically involve immunological methods and assay. A variety of different polyclonal antisera have been prepared against native and fractionated progesterone receptor protein; and against the nuclear binding progesterone receptor complex [Tuohimaa et al., *Biochem. Biophys. Res. Comm.* 119:433 (1984); Renoir et al., *Eur. J. Biochem.* 324:1 (1982); Gronemeyer et al., *J. Biol. Chem.* 260:6916 (1985); Smith et al., *Endocrinology* 122:2816–2825 (1988); Smith et al., *J. Steroid. Biochem.* 30:1–7 (1988); Welgel et al., *Endocrinology* 125:2494–2501 (1989)]. Similarly, some monoclonal antibodies against human and animal progesterone receptor proteins and complexes have been prepared for many different investigational purposes with markedly different degrees of success [Loosfelt et al., *Proc. Soc. Natl. Acad. Sci. USA* 83:9045–9049 (1986); Sullivan et al., *Endocrinology* 119:1549–1557 (1986); Clark et al., *Endocrinology* 121:1123–1132 (1987); Nakoa et al., *Can. J. Biochem. Cell Biol.* 63:33–40 (1985); Hendler and Yuan, *Cancer Research* 45:421–429 (1985); and U.S. Pat. No. 4,742,000].

The common drawback and recurring problem of these known polyclonal and monoclonal antibodies is their uniform and consistent failure to be site-specific or site-selective for a defined domain of PR. This failure, in turn, produces erroneous empirical results and unreliable information- not only for investigational purposes but also in clinical applications of such antibodies for therapeutic purposes. As a major example, the measurement of progesterone receptors in human breast carcinomas has been one aspect of the primary tool and favored diagnostic method (in addition to the measurement of estrogen receptor) for choosing between hormonal and cytotoxic chemotherapy when treating breast cancer patients. A commercially prepared immunoassay kit employing anti-PR antibodies is most commonly used for this purpose [The Abbott PgR-ICA Monoclonal Immunocytochemical Assay; Greene, G. and M. F. Press, *Immunological Approaches To The Diagnosis And Therapy of Breast Cancer* (R. Ceriani, editor), Plenum Publishing Co., New York, 1987, pp 119–135]. Unfortunately, this immunoassay kit employs conventionally obtained monoclonal antibodies prepared against purified whole PR protein for these measurements. These monoclonal antibodies have been found to be frequently unreliable and often insufficiently specific. Clearly, therefore, given all the presently known antibodies, assays, and immunological techniques, one still cannot accurately predict which of these progesterone receptor positive tumors will respond to hormonal treatment.

The causes of the present dilemma are in fact two fold: First is the failure of the known monoclonal antibodies and polyclonal antisera to be sufficiently domain-specific and epitope-selective in order to demonstrate the presence of unfragmented progesterone receptor. Second is the failure (insofar as is presently known) of conventional antibodies to be able to identify the true functional status of progesterone receptor protein using an immunoassay system. It is now clearly apparent to practitioners and clinicians ordinarily skilled in this art that so long as these insufficiently-specific antibodies remain in clinical use, many repetitive failures of the known immunoassay systems will occur; and the clinician's ability to identify that proportion of breast cancer patients which would be sensitive and responsive to hormonal treatment will remain plagued with uncertainty and inaccuracy. For these reasons, the development of domain-specific antibodies which could then be employed within conventional diagnostic immunoassays would therefore be recognized generally as a major advance and fundamental improvement in antibody materials, assay reliability, and therapeutic benefit.

SUMMARY OF THE PRESENT INVENTION

The present invention is a multi-part innovation whose components may be employed individually but which should be employed collectively and cumulatively for maximum use and advantage. The individual component parts include unique prepared immunogens; site-specific monoclonal antibodies; and an improved immunoassay capability employing these site-specific monoclonal antibodies as reagents. The prepared immunogen is able to cause the formation of domain-specific antibodies against a defined region within the progesterone receptor protein molecule and comprises: an oligopeptide having a known amino acid sequence comprised of at least a portion of the amino acids found within one domain of a progesterone receptor protein; and a carrier protein bound to the oligopeptide.

The antibody component includes a monoclonal antibody specific for one epitope within one domain of a progesterone receptor protein.

In addition, an in vitro method to identify the functional status of a progesterone receptor is provided using monoclonal antibodies which identify the presence of native non-transformed 8S form and the activated/transformed 4S form of progesterone receptor protein.

DETAILED DESCRIPTION OF THE FIGURES

The present invention may be more easily and completely understood when taken in conjunction with the accompanying drawing, in which:

FIG. 1 is a representation of the amino acid sequence of the human progesterone receptor;

FIGS. 9A-9F are graphs illustrating the binding of PR to increasing concentrations of the monoclonal antibody.

DETAILED DESCRIPTION OF THE PREFERRED EMBODIMENTS

Figure 3:
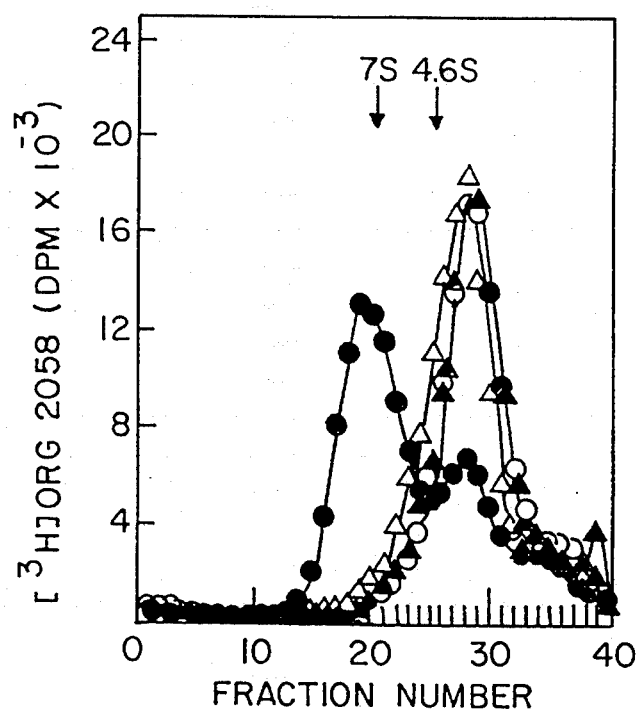
FIG. 3 is a graph demonstrating sucrose density gradient analysis of one monoclonal antibody.

The present invention as a whole is based upon the unique approach of developing site-specific monoclonal antibodies against one prechosen domain of progesterone receptor protein. The monoclonal antibodies are used to identify the presence of a single epitope or antigenic determinant within the prechosen domain; and to detect both the non-transformed, native, and the transformed functional states of progesterone receptor in vitro. On this detection basis, the user is able to determine whether the PR is present in an intact state within the molecule; or is in an altered, fragmented, or degraded state which is non-functional. The invention, therefore, includes specifically prepared immunogens; monoclonal antibodies which bind specifically to a single epitope associated with the DNA-binding domain of PR; and immunoassays employing these epitope-specific antibodies with cellular samples on a functional correlative test basis.

It will be noted and appreciated that the present invention overcomes several major impediments and disadvantages normally encountered in the production and use of specific antibodies. These include:

1. Since oligopeptides of known amino acid composition are employed as the hapten within the prepared immunogen, there is no longer any need for purification of PR, particularly human PR, for immunization purposes; thus, a task which normally requires large resources and considerable amounts of tissue is eliminated.

2. The present invention allows the user to preselect for a single epitope located at or near the one domain intended to be detected by the antibody. Previous approaches and techniques for raising antibody typically utilized either the entire progesterone receptor protein or the complete hormone/receptor complex as the immunogen—neither of which provides any site specificity properties or capabilities whatsoever. In those few instances where a single synthetic immunogen was reportedly employed as the antigen, only a limited-use polyclonal antisera was obtained; a mixed antisera demonstrably unable to detect the native, non-transformed PR molecule. In comparison, the unique monoclonal antibodies described herein are able to detect a single epitope in both the native (8S) and transformed (4S) forms of PR.

3. The present invention precludes the binding of the site-specific monoclonal antibody to a PR protein when present in an altered, non-functional, or modified state. The monoclonal antibodies may thus be utilized to identify and empirically evaluate the functional integrity of both native and transformed forms of progesterone receptor.

To fully appreciate the present invention, it is useful to focus on a single kind of progesterone receptor protein, recognizing that the characterization of the one PR may properly be extended to include all other types and sources of PR protein generally. For this reasons, the remainder of this description and the experiments and empirical data which follow hereinafter are limited to the use of human progesterone receptor (hereinafter "hPR"). For this purpose also, all the presently available information regarding the primary amino sequence and the individual functional domains of human progesterone receptor protein have been employed. Nevertheless, it will be clearly and explicitly understood, that the scope of the present invention encompasses the ability to prepare site-specific antibodies against PR from all presently known sources and origins, whether human or animal.

Oligopeptides

As regards human progesterone receptor protein and its native (8S) and/or functional (4S) states, it will be recognized that the human receptor molecule is a single polypeptide comprising amino acids in sequence in which the DNA-binding domain encompasses the cysteine-rich amino acid segment at about positions 567-644 respectively. This central domain is a critical region of the human PR because these amino acid sequences collectively provide the means and capability for the entire PR molecule to bind to genomic DNA in vivo. It is desirable, therefore, that at least a portion of the amino acids adjacent to or actually within this central DNA-binding domain provide the oligopeptides which are to serve as haptens for raising site-specific monoclonal antibodies in accordance with the present invention.

As described in detail hereinafter, an oligopeptide having amino acid sequences identical to those amino acids found at positions 533–547 of human progesterone receptor were prepared and purified. This individual oligopeptide (Nos. 533–547) was first linked to an antigenic protein carrier such as keyhole limpet hemocyanin; and then was used as a prepared immunogen to produce antibodies against a single epitope lying adjacent to the DNA-binding domain (Nos. 567–644), specifically.

For purposes of practicing the present invention, however, it is not necessary that this specific hPR amino acid sequence (Nos. 533–547) be employed when preparing the immunogen. To the contrary, for general purposes, it is required only that a single oligopeptide be chosen whose amino acid sequence corresponds to at least one epitope of the many created by the entire amino acid sequence of a known progesterone receptor protein such as hPR (Nos. 1–933). Any amino acid segment able to function as a hapten—thereby providing one specific epitope or site-specific binding capability for the resulting antibody—is suitable for use. Moreover, although the chosen oligopeptide described herein is approximately 15 amino acids in length, there is no requirement that any other chosen polypeptide chain conform to this length or three-dimensional shape for purposes of preparing the immunogen. In general, however, it is desirable that the chosen oligopeptide be at least in the order of about 5–7 amino acids in length as the minimum segment size typically able to serve immunologically as a hapten. Nevertheless, any series of amino acids in sequence of any size or length which is able to provide the necessary hapten function and site-specificity for the prepared immunogen is suitable and deemed to be within the scope of the present invention.

In addition, although it is most desirable that the amino acid composition of the oligopeptide be in fact identical to the true, naturally occurring amino acid sequence within the chosen domain or region, this is not deemed to be an absolute requirement. It is expected that substantial variation of the amino acid sequencing differing from that found within the region of the PR molecule is permissible; nevertheless, it is most desirable and most effective for the chosen amino acid sequence to be completely or very nearly identical to sequences adjacent to the DNA-binding domain particularly when the oligopeptide size is of minimal length. The reasons for this preference are given below.

Choice Of Oligopeptide for Test Purposes

Although oligopeptides can be purposely synthesized to represent any amino acid sequence found within the entire length of the PR molecule; and although each of these can be joined to a carrier molecule to form a prepared immunogen; and even if a wide variety of diverse monoclonal antibodies were elicited in vivo by these prepared immunogens individually—there remains the overriding question of whether the specific amino acids comprising the single epitope within the native PR molecule are spatially available for immunoreaction with the elicited monoclonal antibodies under test conditions. It must be recognized and appreciated that the native, non-transformed (8S) form of hPR and the transformed, functional (4S) form of hPR exist as three-dimensional entities whose secondary and tertiary structures compel conformational changes—i.e., the internalization and/or externalization of many specific amino acid sequences comprising the primary structure for the molecule. Correspondingly, although found analytically to be part of the PR structure, the three-dimensional internalization of some oligopeptide sequences spatially prevents them from reacting and binding with monoclonal antibodies which are demonstrably specific for these same amino acid sequences.

For this reason, although selective, single-epitope monoclonal antibodies demonstrably specific against those amino acid sequences representative of the cysteine-rich DNA-binding domain of hPR have been empirically prepared—several of these epitope specific monoclonal antibodies were found to be unable to react in vitro with either the native, non-transformed (8S) hPR or with the transformed, functional (4S) form of hPR. Thus, as will be described, the amino acid sequences spanning Nos. 597–611 and Nos. 764–779 of the human progesterone receptor provided prepared immunogens and antisera which were unable to react with either the native (8S) or the transformed (4S) forms of hPR subsequently; while the immunogens comprising the amino acid sequence spanning Nos. 533–547 yielded monoclonal and polyclonal antibodies which were immunochemically reactive with both the native (8S) and transformed (4S) forms of hPR.

Accordingly, it is deemed to be far more desirable when choosing an epitope for raising site-specific monoclonal antibodies, that the chosen amino acid sequence or oligopeptide be one which is not spatially internalized or conformationally altered within the tertiary structure of the PR molecule in vivo. As presently understood, it appears that the DNA-binding domain or "C" region of hPR is conformationally altered in the native, non-transformed (8S) form and in the transformed, functional (4S) form prior to actual contact with the intracellular nucleic acids. Nevertheless, the epitope-specific monoclonal antibodies site-selective for the amino acid sequence comprising Nos. 533–547, respectively, were able to bind to and immunochemically react with the 8S and 4S forms because the oligopeptide sequence representative of the amino acids at Nos. 533–547 lies adjacent to and immediately before the DNA-binding region itself. Thus, the amino acids at Nos. 533–547 appear to be part of an externalized "bridge" sequence between the aminoterminal domain and the DNA-binding domain as such; and empirically also appear to be unaltered conformationally within the tertiary spatial structure considered normal for both the (8S) native and (4S) transformed states of hPR. The proper choosing of an epitope thus is a major consideration in arriving at an effective immunoassay.

Immunogens

Once the desired oligopeptide composition has been chosen, it is preferably synthesized using conventional methods and chemically coupled to protein or non-protein carriers to form the prepared immunogen. The suitable carriers available for this purpose are conventionally known and available in great variety from diverse sources. The only requirements regarding the characteristics and properties of the carriers are: First, that the carrier be in fact antigenic alone or in combination with the chosen oligopeptide; and second, that the protein or non-protein carrier be able to present the chemically bound oligopeptide as an immunogen after administration in vivo such that antibodies specific against a single epitope of at least one domain of the PR molecular are produced. Clearly, as in the experiments described hereinafter, the preferred choice of protein carrier for immunization purposes is keyhole limpet hemocyanin (hereinafter "KLH"). However, any other carrier protein compatible with the host to be immunized is also suitable for use. Examples of such other carrier proteins include bovine serum albumin, gelatin, thyroglobulin, and the like. Alternatively, glass beads are an example of useful nonprotein carriers.

Immunization Procedure

All immunizations and immunization procedures are performed in a conventionally known manner. It is expected that under certain use conditions, known adjuvants will be employed in combination with the prepared immunogens. Alternatively, the prepared immunogens may be used alone and administered to the host in any manner which will initiate the production of specific antibodies in vivo.

In addition, the isolation of antibody containing sera or of antibody producing cells follows the conventionally known techniques and processes for this purpose. Similarly, the preparation of hybridomas follows the best practices developed over recent years for this specific purpose [Marshak-Rothstein et al., *J. Immunol.* 122:2491 (1979)]. A detailed disclosure of the preferred techniques and procedures are provided within the experimental section which follows hereinafter.

Monoclonal Antibodies

Once obtained from their living hosts, the monoclonal antibodies should be evaluated and verified for their ability to bind specifically with a single epitope adjacent to or lying within one domain of a PR molecule. The elicited monoclonal antibodies empirically evaluated hereinafter have been found to bind specifically with the amino acid sequence spanning Nos. 533–547 of human PR in the (8S) and (4S) forms. This monoclonal antibody therefore is operative to identify the presence of human PR protein in its various states—be they the native (8S) form or the activated/transformed (4S) form.

When utilized within assay procedures for this purpose, these epitope-specific monoclonal antibodies will accurately detect the presence of unaltered PR intracellularly whether in the non-transformed or transformed functional state. Within this context, a functional PR molecule represents and defines the ability of the 4S form of progesterone receptor to bind to genomic DNA. The obtained monoclonal antibodies are site-specific in their properties; and they will not bind in vitro to a degraded, fragmented, or modified form of hPR regardless of its sedimentation properties. Accordingly, the monoclonal antibodies will serve to identify accurately the presence of normal progesterone receptors within the cells or tissues being evaluated.

One valuable application of this ability to identify normal human progesterone receptor in a cellular sample is the use of such epitope-specific antibodies in assay procedures for the accurate quantitation of cytosolic progesterone receptors in breast cancer tissue samples. By employing these monoclonal antibodies within individual assays, the resulting data can be used to correlate not only the presence of progesterone receptors as such; but also to determine whether the progesterone receptors within the tissue obtained from a single source or patients are normal or abnormal—i.e., functional or non-functional. Moreover, if the PR in a tissue sample is found to be primarily normal (rather than fragmented, degraded, or unable to bind to nucleic acids), the identified normal PR can subsequently be quantified as being in either 8S or 4S form by sucrose density gradient analysis.

To demonstrate the uses of the monoclonal antibodies for such assay purposes, preferred protocols are provided which will merely illustrate the range of methods and manipulative steps able to be employed in the performance and the utilization of immunoassays. It will be expressly understood, however, that the procedural steps described hereinafter are merely representative of the nature and manipulative steps employed within immunoassays generally. The described protocols are not self-limiting and are not restricted to only the described manipulative steps and the test conditions employed. To the contrary, it is deemed and expected that a wide variety of homogeneous and heterogeneous immunoassay systems may be employed; that the parameters of concentration, volume, temperature, and choice of reagents can be varied extensively at will; that the identifying labels used with the monoclonal antibodies in such assays may be either isotopic or non-isotopic in nature; and that the protocols might be embodied as kits or other test apparatus in commercially saleable form rather than individually prepared reagents and reactants. The present invention presumes and incorporates by reference any conventionally known immunoassay technique, procedure, protocol, substrate, and any other non-decisive factors or parameters—all of which may be varied and altered within any given immunoassay procedure. None of these are deemed to be essential or dominant criteria when performing the methods of the present invention.

Accordingly, for illustrative purposes only, preferred protocols utilizing epitope-specific monoclonal antibodies selective against the amino acid sequence (Nos. 533–547) adjacent to the DNA-binding domain of human progesterone receptor are given hereinafter.

Preferred Progesterone Receptor Assay Protocol

Buffers

Buffer TEGT contains 50 mM Tris-HCl, 10% (v/v) glycerol, 1 mM ethylenediamine tetraacetic acid (EDTA), 10 mM monothioglycerol, and 0.02% sodium azide (pH 7.4 at 2° C.).

Buffer TEGT/Mo contains 10 mM sodium molybdate in buffer TEGT.

Buffer TEGT/Mo/KCl contains 0.4M KCl in buffer TEGT/Mo buffer.

Preparation of Cytosol Fractions

Frozen human breast cancer tissue is pulverized, weighed, and placed in a test tube on ice. Unless otherwise stated, all manipulations are performed at 0–4° C. Ice cold buffer TEGT/Mo containing 0.5 mM phenylmethyl sulphonyl fluoride and 1.0 ug/ml leupeptin (pH 7.4 at 0–2° C.) is added to the tissue in a 4:1 vol/wt and homogenized with a polytron Pt-10 homogenizer using 5 second burst and 30 second cooling periods between bursts. The homogenate is then transferred into ultracentrifuge tubes; and centrifuged at 100,000×gravity for 45 minutes at 2° C. The high speed supernatant fraction (or cytosol) is then transferred to a clean tube and placed on ice.

Incubation of the Cytosol With Radiolabelled Progesterone

A commercially prepared radiolabelled progesterone analogue, [3H]-ORG 2058 (40–60 Ci/mmol) and unlabelled ORG 2056 (40 to 60 Ci/ml) sold by Amersham Corp., Arlington Heights, Ill., are preferred for use in this assay. Aliquots of the cytosol are then incubated with 10 nM of [³H]-ORG 2058 at 0° to form the progesterone receptor/progesterone complexes. To determine the nonspecific binding, parallel aliquots of cytosol were incubated with [³H]-ORG 2058 and a 100-fold molar excess of unlabelled ORG 2058.

Removal of Unbound Radioactive Progesterone

At the end of the incubation period, unbound radioactive progesterone was removed with dextran coated charcoal ("DCC") in the following manner. A DCC suspension (0.5% charcoal; 0.05% dextran) in Buffer TEGT is centrifuged at 2,000×gravity for 10 minutes and the supernatant discarded. The incubated cytosol samples are then transferred into individual DCC pellets, mixed, and kept on ice for 20 minutes with intermittent mixing. The resulting suspensions are then centrifuged at 2,000×gravity for 10 minutes. The supernatants are used as the source of labelled cytosol for monoclonal antibody receptor interaction subsequently.

Determination of Progesterone Receptors by An Enzyme Immunoassay

Microtiter 96-well plates are used. Aliquots of bovine serum albumin conjugated oligopeptide comprising a defined epitope of PR (10 ng/well) in 50 ul of phosphate buffered saline are pipetted into each well and allowed to bind at 0° C. for 16 hours. The wells are then coated with 200 ul of 2% bovine serum albumin (BSA) in phosphate buffered saline (PBS) for 1-2 hours at 25° C. The plates are then washed with PBS three times and used for competitive binding assay.

An aliquot of the epitope-specific monoclonal antibody is diluted 1:2,000 with BSA/PBS; and 50 ul are incubated for 16 hours at 0°-2° C. with increasing volumes of the human breast tissue cytosol (10 to 200 ul). This allows the monoclonal antibody-receptor protein interaction to form an epitope-specific antigen/antibody complex. The antibody/cytosol mixture is then added to the wells of the microtiter plate and incubated at 0°-2° C. for additional 16 h. The individual wells are then washed three times with PBS; a secondary antibody previously conjugated to alkaline phosphatase is added in 1:5,000 dilution in BSA/PBS to each well; and the reaction mixture incubated at 25° C. for 2 h. The unbound antibody is then removed and the wells washed three times in PBS. An enzyme substrate for alkaline phosphatase is then added to each well and incubated at 25° C. for 30 minutes in the dark. The color reaction is then stopped by the addition of 0.5 N NaOH. The color product of the reaction is measured by ELISA microtiter reader at 450 nm.

Control incubations are made in the absence of cytosol. This allows measurement of all the epitope-specific monoclonal antibody bound in the reaction mixtures. Nonspecific binding is determined by omitting the primary monoclonal antibody. Additional controls are provided by wells that were coated with BSA only and do not contain any oligopeptide. Calf uterine cytosol with known progesterone receptor content is used as external standard to evaluate the reproducibility of the assay.

Determination of the Functional Integrity of the Progesterone Receptor

An aliquot of the cytosol to be tested is labelled with radioactive ORG 2058 as described above and is incubated with 25 ug of the epitope-specific monoclonal antibody at 0°-2° C. for 4-16 in the presence of Buffer TEGT/Mo/KCl. The total sample is then layered together with 14C-labelled BSA and human gamma globulin using a 5-20% sucrose density gradient (made in Buffer TEGT/Mo/KCl using 4 ml polyallomer ultracentrifuge tubes). The gradients are centrifuged at 50,000 rpm in a SW60 Beckman rotor for 18 h at 2° C. The gradients are then fractionated into 0.1 ml individual fractions; 0.5 ml of water and 4 ml of Liquiscint are then added. The samples are then counted for radioactivity. The intact progesterone receptor binds to the monoclonal antibody and sediments in the 9-10S and 4S regions of the gradient. Progesterone receptors with defective, missing, or altered DNA binding domain will not interact with the epitope-specific monoclonal antibody and, therefore, will not sediment at all.

EMPIRICAL DESCRIPTIONS

To further document and demonstrate the individual parts of the present invention and the major advantages and abilities provided by the invention as a whole, a variety of different experiments were performed and the resulting data recorded. These empirical experiments and data are provided in detail hereinafter in order that the properties, characteristics, uses, and advantages of each component part may be properly appreciated and understood. It will be recalled, however, that These experiments are directed to only human progesterone receptor rather than PR from animal sources; and that the specific embodiments, procedures, modes of preparation, and immunoassays described herein are merely illustrative and representative of the wide diversity and totality of embodiments encompassed within the scope of the present invention.

I. Preparation of Synthetic Oligopeptides and Immunogens Representative of a Single Epitope in Human Progesterone Protein The DNA-binding domain of human progesterone receptor is encompassed by the cysteine-rich central region in the native protein which spans the amino acids at about Nos. 567-644. FIG. 1 illustrates the chosen peptides with amino acid sequence 533-547 lying adjacent to the DNA-binding domain which is believed to be one of the bridging sequences lying between and joining the amino-terminal domain and the DNA-binding domain. The individual amino acids are identified using the single letter amino acid code system, a listing of which is given by Table 1 below.

The segment of amino acids at positions Nos. 533-547 within normal hPR is: GLPQVYPPPYLNYLRP.

In addition, FIG. 1 also depicts the two other peptides chosen from human progesterone receptor with amino acid sequences 597-611 and 764-779 respectively. It is noted that Nos. 597-611 lie well within the DNA binding domain before the hinge region (D); while Nos. 764-779 lie within Region E, the general progesterone binding domain.

The 597-611 amino acid segment is: GQHNYL-CAGRNDCIV.

The 764-779 amino acid sequence is: GWRSYKHVSGQMLYF.

For comparative purposes, immunogens comprising each of these oligopeptides individually were prepared. Each of these oligopeptides is deemed to include at least one epitope of human progesterone receptor protein.

Table 1

SINGLE LETTER CODE SYSTEM*

A = alanine
B = asparagine or aspartic acid

C=cysteine
D=aspartic acid
E=glumatic acid
F=phenylalanine
G=glycine
H=histidine
I=isoleucine
K=lysine
L=leucine
M=methionine
N=asparagine
O=glutamine
P=proline
Q=glutamine
R=arginine
S=serine
T=threonine
V=valine
W=tryptophan
Y=tyrosine
Z=glutamine or glutamic acid
*Stryer, L., *Biochemistry*, W. H. Freeman and Co., New York, 1988.

Synthesis of Oligopeptides

Each oligopeptide sequence disclosed above and by FIG. 1 was prepared using conventionally known solid phase peptide synthesis methods [Merrifield, R. B., *J. Am. Chem. Soc.* 85:2149 (1963)]. Once synthesized, each oligopeptide was individually purified by gel filtration and analyzed for purity by HPLC. Analysis of the amino acid composition correlated well with the primary sequence. Each peptide sequence contained one [$^3$H]-labelled amino acid as a tracer. This provided the means for determining the efficiency of coupling to the various carrier proteins.

Reagents

Isotopes and Chemicals

[$^3$H]-Estradiol (40–60 Ci/mmol) ([$^3$H]-E$_2$), [$^3$H]-ORG 2058 (40–60 Ci/mmol), [$^3$H]-mibolerone (70–85 Ci/mmol), [$^3$H]-dexamethasone (95 Ci/mmol); unlabelled mibolerone and ORG 2058 were obtained from Amersham, Arlington Heights, Ill. Unlabelled estradiol was obtained from Steraloids, Wilton, N.H. Unlabelled dexamethasone was obtained from Sigma Chemical Co., St. Louis, Mo. All other chemicals were reagent grade and were obtained from commercial sources.

Buffers and Solutions

Phosphate buffered saline (PBS): (0.2 g KH$_2$PO$_4$, 8 g NaCl, 0.16 g Na$_2$HPO$_4$.7H$_2$O in one liter of distilled water, pH 7.5). Buffer TEGT: 50 mM Tris-HCl, 10% (vol/vol) glycerol, 1 mM EDTA, 10 mM monothioglycerol and 9.92% sodium azide, pH 7.4 at 2° C. Buffer TEGT/Mo: buffer TEGT containing 19 mM sodium molybdate. Buffer TEGT/Mo/KCl: buffer TEGT/Mo containing 9.4M KCl.

Coupling of Oligopeptides to Carrier Proteins

To prepare effective immunogens, oligopeotide of human PR comprising a single epitope were individually coupled to known carrier proteins to form antigenic immunogens. The carrier proteins of choice were keyhole limpet hemocyanin (hereinafter "KLH") and bovine serum albumin (hereinafter "BSA"). The KLH-coupled peptides were used as immunogens while the BSA-coupled peptides were used only for screening assays. This coupling procedure was performed as follows.

KLH and BSA were dissolved in phosphate buffered saline (PBS: 0.2 g KH$_2$PO$_4$, 8 g NaCl, 2.16 g Na$_2$HPO$_4$.7H$_2$O in one liter of distilled water, pH 7.5) to give a final concentration of 1 mg/ml. One hundred mg of each peptide sequence was then dissolved in 10 ml of KLH solution and 50 mg of each peptide was dissolved in 5 ml of BSA solution. The pH of the mixtures was adjusted to 9 with 0.1M LiOH. The coupling of the individual peptides to the carrier proteins was initiated by dropwise addition of 6.25% glutaraldehyde to achieve a final concentration of 1% glutaraldehyde. Each mixture was then incubated at 0°–4° C. for 1 hour with gentle agitation. Aliquots (50–200 ul) were then removed and used to determine total peptide concentration by radioactivity counting. The remainder of each mixture was then transferred to dialysis tubes and dialyzed extensively against four changes of PBS. Aliquots were then removed after dialysis and counted to determine the efficiency of coupling. The remaining dialyzed material was divided into 1 ml aliquots and frozen at −80° C. until needed.

II. Ability of Oligopeptide Immunogens to Induce an Antibody Response In Vivo

Immunization of Rabbits

New Zealand White female rabbits (7–9 lbs) were obtained from Pine Acre Rabbitry (Norton, Mass.). Before immunization, serum was collected from each rabbit by bleeding through the ear artery and designated as pre-immune serum. One day later each animal was injected subcutaneously (sc) at multiple sites along the back with a total of 1 ml of an emulsion made by mixing equal volumes of complete Freund's adjuvant and a KLH-conjugated peptide. The final emulsion contained 500 ug/ml of the desired peptide. After three weeks the animals were boosted with the antigen in incomplete Freund's adjuvant. Two weeks after the booster shots the animals were bled, the sera were collected, and tested for the presence of antipeptide antibodies by enzyme-linked immunosorbent assay (ELISA).

Immunization of Mice

Three groups (5 animals per group) of female mice 6–8 weeks old were immunized by subcutaneous injection with 100 ug of the peptide-KLH conjugate emulsified in complete Freund's adjuvant. Two booster injections were given at 3 week intervals. Serum samples were collected 10 days after immunization and tested for specific antibodies to progesterone receptors by sucrose density gradient analysis. Mice with antiserum that recognized the native (8S) progesterone receptor (i.e., PR which binds steroids) were injected interperitoneally (ip) one month later with 100 ug of the immunogen in PBS; after three days the animals were sacrificed, the spleen was removed and used for fusion.

Antibody Binding Capability

Because of our interest in obtaining only antibodies that recognize the undenatured (native, functional) and not the denatured form of the PR, sera from immunized mice and rabbits were screened for antibodies that recognized the progesterone binding form of PR. In preliminary experiments we determined that antisera from both rabbits and mice recognized PR not only from human breast tissue but also from calf uterine cytosol, using sucrose density gradients. Thus, calf uterine tissue was employed as a source of PR for further characterization of these antibodies, since this tissue is readily available and is a rich source of PR.

As an example, antisera from immunized mice were tested for their ability to increase the sedimentation rate of PR on sucrose density gradients containing 0.4M KCl. The results are graphically summarized by FIG. 2 Aliquots of cytosol labelled with [$^3$H]-ORG 2058 in the absence (total binding) or the presence (nonspecific binding) of unlabelled ORG 2058 were treated with DCC and incubated for 16 h at 4° C. with normal mouse serum (control). At the end of the incubation, rabbit antimouse IgG was added and the samples were kept for an additional 4 h at 0° C. The immunoprecipitated complexes were collected by centrifugation and washed three times with PBS. Bound radioactivity was extracted with ethanol and the total extract was counted. To insure that PR is precipitated specifically by the antibodies, additional antibodies prepared against the human estrogen receptor were used as control.

Figure 2:
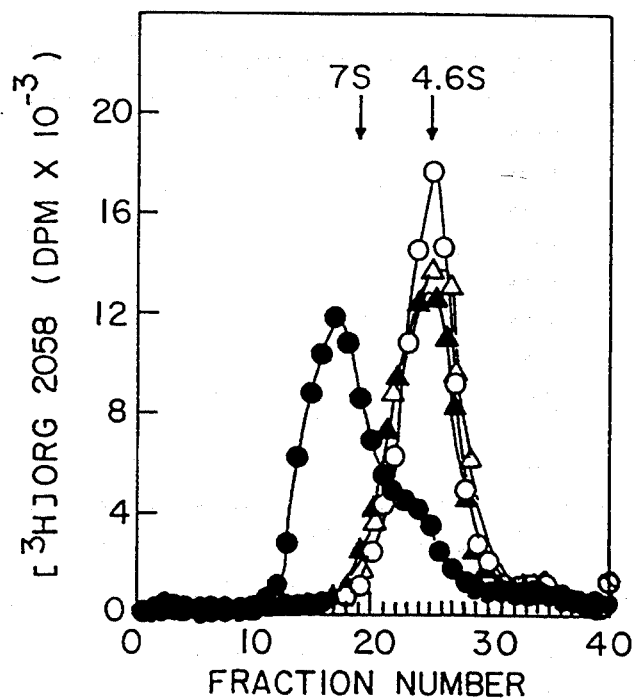
FIG. 2 is a graph illustrating the interaction of different antisera raised against specific oligopeptide sequences from hPR.

As seen within FIG. 2, pre-immune serum did not alter the sedimentation rate of the PR (FIG. 2, open circles). Antisera from animals immunized with oligopeptide Nos. 533-547 tested positive against undenatured PR as shown by the increased sedimentation rate of the labelled hormone receptor complex (FIG. 2, solid circles). In contrast, antisera prepared against oligopeptide Nos. 597-611 (open triangles) and oligopeptide Nos. 764-779 (solid triangles), although eliciting antibodies that recognized BSA-conjugated peptide by ELISA, failed to recognize the undenatured form (8S) of PR on sucrose density gradients and by immunoprecipitation assay. Thus, only those antibodies elicited by the KLH-peptide Nos. 533-547 were further characterized.

III. Isolation of Monoclonal Antibodies Capable of Binding to a Specific Epitope of Human Progesterone Receptor Cells and Media Cultures of mouse myeloma cell line SP2/0 were maintained in Dulbecco's modified Eagle's medium (DME) (GIBCO, Grand Island, N.Y.) supplemented with fetal calf serum (FCS, 20%) (Hazelton, Lenexa, Kans.), penicillin (10 units per ml), streptomycin (100 ug/ml), nonessential amino acids (GIBCO), and glutamine (580 ug/ml). After fusion the cells were plated in DME supplemented with hypoxanthine (0.1 mM), aminopterin (0.4 uM), thymidine (3 uM), and concanavalin A (conA) conditioned medium (10%) (HAT medium). DME medium supplemented with hypoxanthine and thymidine (HT medium) was also prepared for later use. ConA conditioned medium was obtained by incubating BALB/c mouse spleen cells ($3 \times 10^6$ cells/ml) with conA (2 ug/ml), at 37° C. in DME under 5.6% $CO_2$ for 4 h. The tissue culture supernatants were separated by centrifugation and stored at 4° C.

Cell Fusion

Cell fusion was carried out by the method of Marshak-Rothstein et al. [*J. Immunol.* 122:2491 (1979)]. Briefly, mouse spleens were excised; the fat and mesenteric tissues were removed quickly; and a single cell suspension was made by squeezing the spleen between two glass slides in Hank's balanced salt solution (HBSS) buffered with 0.01M phosphate, pH 7.2. Red blood cells were lysed by brief incubation in ammonium chloride lysis buffer. Spleen cells ($5 \times 10^7$ cells) were mixed with SP2/0 cells ($5 \times 10^6$ cells) in round bottom tubes and pelleted at $700 \times g$ for 5 min at 22° C. The cells were resuspended in serum-free DME and centrifuged. After removal of the supernatant, the cell pellet was resuspended for six minutes in 0.5 ml of polyethylene glycol 1,500 (PEG, 30% v/v) (Baker Chemical Co., Phillipsburg, N.J.), followed by addition of 4 ml of serum-free DME to dilute out the PEG to a final concentration of 3.3%. The cell suspensions were transferred into petri dishes ($100 \times 17$ mm) and DME containing 20% FCS was added and the cultures were kept at 32° for 24 h under 5.6% $CO_2$. The cells were then pelleted and resuspended in HAT conditioned medium ($1 \times 10^6$ cells/ml). Aliquots of the cell suspension (0.1 ml) were dispensed into 96-well flat bottom microtiter dishes and incubated at 37° C. Seven days later the hybridoma cells were treated with 0.1 ml of conditioned media (DME, HT). After another two days, the resulting hybridomas were screened by enzyme-linked immunosorbent assay (ELISA) against BSA-conjugated oligopeptides.

The isotype of each monoclonal antibody was determined by ELISA. Microtiter plates coated with the immunogenic oligopeptide were incubated with aliquots of the spent media from the hybridoma. Bound antibody heavy chain class was determined by addition of goat-antimouse isotyping reagents (Southern Biotech, Birmingham, Ala.) diluted 1:1,000 in PBS-0.2% BSA, followed by alkaline phosphatase conjugated rabbit-antigoat secondary antibody and the substrate.

Cloning by Limiting Dilution

Cells from wells that tested positive by ELISA were cloned by limiting dilution. Cells were diluted to 1, 0.3, and 0.1 cell equivalent/100 ul in DME containing 20% fetal calf serum and BALB/c peritoneal exudate cells ($5 \times 194$ cells/ml) and plated into 96-well microtiter plates. After ten days, wells with single clones were identified by microscopic examination and tested for the presence of antibodies by ELISA. Clones that tested positive were expanded in large flasks, spent media were collected and used for immunoprecipitation assay of PR. The cells were grown and either used for production of ascites fluid or frozen for later use.

Ascites Production

Female mice (BALB/c $\times$ A/J)F$_1$ were injected ip with pristane (9.5 ml) and seven days later the animals were injected with $1 \times 10^6$ hybridoma cells in 9.2 ml of PBS. Ascites fluid was collected 7-19 days later by insertion of a needle into the peritoneal cavity. The fluid was clarified by centrifiguation at $799 \times g$ for 19 min, divided into several vials, and kept frozen at $-80°$ C. until use.

IV. Properties and Characteristics of Epitope-Specific, Anti-Human Progesterone Receptor Monoclonal Antibodies Monoclonal Antibodies After cell fusion the tissue culture supernatants were first screened with oligopeptide (Nos. 533-547) conjugated to BSA by the ELISA technique and the positive clones were rescreened by immunoprecipitation assay using [$^3$H]-ORG 2958 PR complexes. Spent media from several clones (identified as PR-AT Nos. 4.14, 4.12, 4.17, and 4.19) precipitated undenatured PR. These clones were further tested for their interaction with PR using sucrose density gradient analysis, since this would allow the selection of antibodies with high affinity.

Sucrose density gradients (5-20%) were prepared with TEGT/Mo buffer with or without 0.4M KCl for each experiment. Samples to be analyzed were layered on the gradient together a with C-labelled bovine serum albumin (4.6 S) as an internal sedimentation marker. The gradients were centrifuged at 50,000 rpm in a SW60 rotor for 18 h at 2° C. Gradients were then fractionated into individual 0.1 ml fractions; scintillation fluid was added to each sample; and radioactivity counted.

As shown in FIG. 3, the labelled progesterone receptor complexes sediment as 4S entity in the presence of 0.4M KCl (open circles). Incubation of PR with monoclonal antibody PR-AT 4.14 increased the sedimentation rate of PR (from 4S to an 8S) in the presence of KCl, illustrating binding of the PR to the antibody with high affinity. Other monoclonals which tested positive by immunoprecipitation and ELISA assays did not increase the sedimentation rate of PR (FIG. 3, open and solid triangles). To further characterize the monoclonal antibodies, ascites fluids were used to analyze PR-antibody interactions.

Figure 4A:
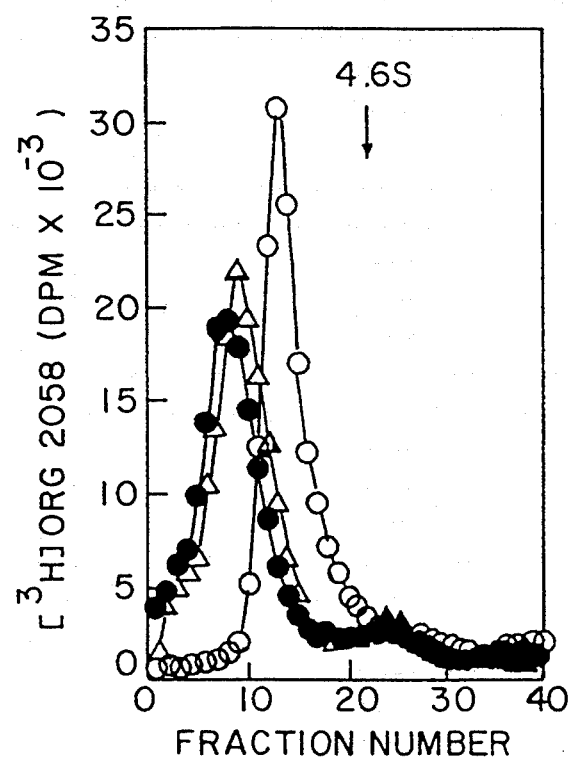
FIGS. 4A and 4B are graphs illustrating the interaction of a monoclonal antibody with molybdate-stabilized untransformed, and salt-transformed PR.
Figure 4B:
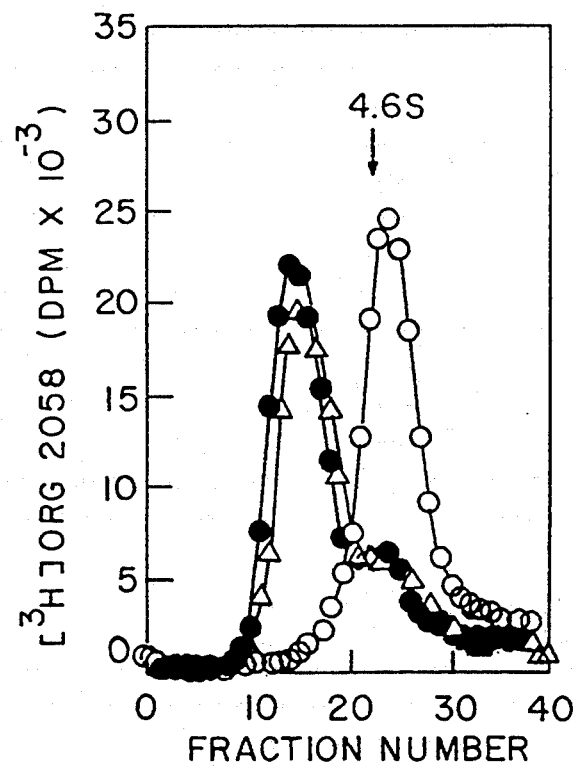

The high affinity monoclonal antibody (PR-AT 4.14) produced against peptide sequence Nos. 533-547 was tested for its ability to bind to the molybdate-stabilized untransformed 8S and salt transformed (4S) PR. As shown in FIG. 4A (open circles), in the absence of the monoclonal antibody, the untransformed PR sedimented at 8S on sucrose density gradients prepared in low salt buffer containing sodium molybdate. In the presence of the epitope-specific monoclonal antibody, the PR sedimented as a complex in the 10S region of the gradient (FIG. 4A, solid circles). This indicated that the antibody bound to the molybdate-stabilized untransformed PR with high affinity. PR prepared and labelled in low salt buffer and then incubated with the antibody at 0°–4° C. sedimented as a 10S complex when analyzed in the presence of 0.4M KCl. These observations are not surprising since this specific antibody was raised against a peptide sequence (533–547), in the amino terminal region located 19 amino acids away from conserved cysteine residue of the DNA-binding domain. Thus, it is deemed that this positional location is accessible to the antibody when PR is in the untransformed state. Furthermore, it is believed that this domain is neither masked nor altered by the binding of heat shock proteins (which are known to be associated with untransformed steroid receptors) since the molybdate-stabilized, untransformed 8S complex is recognized by the monoclonal antibody. Pre-incubation of the labelled cytosol with 0.4M KCl to induce receptor transformation from the 8S to the 4S form followed by incubation with the monoclonal antibody, increased the sedimentation rate of the 4S complex to 8S as seen in FIG. 4B. This result demonstrates that the antibody bound to the transformed PR. Once salt transformed, the PR bound to the monoclonal antibody and sedimented as a large molecular weight complex entity regardless whether it was analyzed in the presence of KCl (FIG. 4B, solid circles) or in the absence of KCl (FIG. 4B, open triangles).

Site-Specificity

Figure 5A:
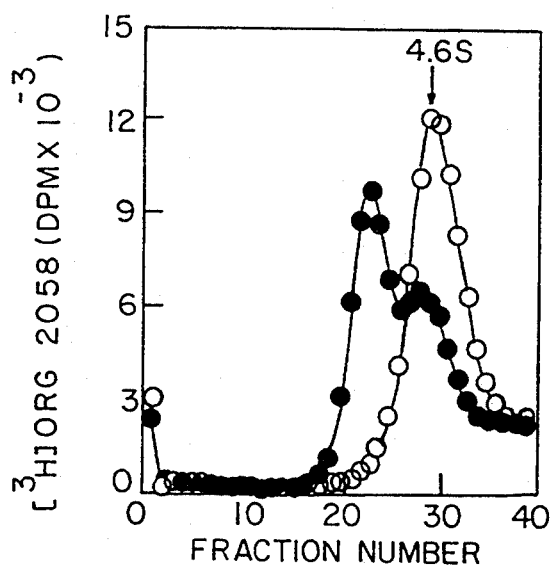
FIGS. 5A-5D are graphs illustrating site-specificity of the monoclonal antibody via sucrose density gradient analysis.
Figure 5B:
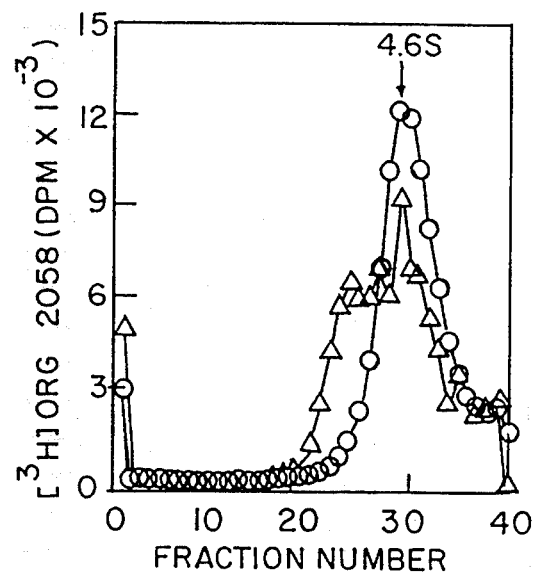
Figure 5C:
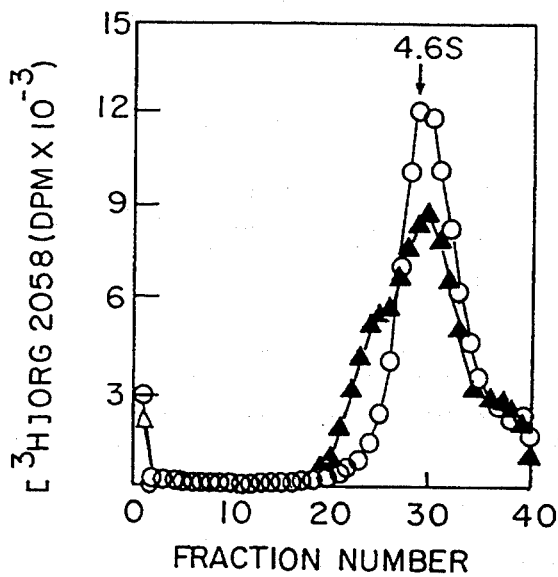
Figure 5D:
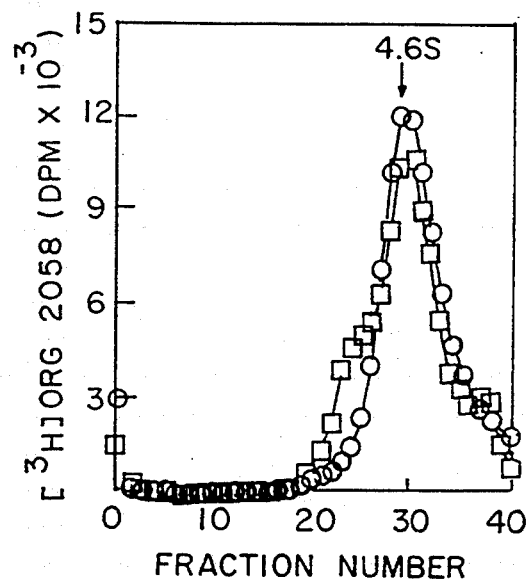

The site-specificity of the monoclonal antibody to the epitope spanning amino acids 533-547 was tested by the ability of the unconjugated oligopeptide to compete for PR binding to the antibody. As shown in FIG. 5A (open circles), PR alone sedimented at 4S on SDG containing 0.4M KCl while in the presence of the antibody PR sedimented at 8S (FIG. 5A, solid circles). When the monoclonal antibody was initially incubated with 1 ug of the oligopeptide for 2 h and then reincubated with PR, a decrease in the fraction of PR sedimenting at the 8S was observed, suggesting that the oligopeptide is competing for the PR binding to the antibody (FIG. 5B, open triangles). When the oligopeptide concentration in the incubated mixture was increased to 10 ug (FIG. 5C, solid triangles) or to 50 ug (FIG. 5D, open squares), the fraction of PR sedimenting in the 8S decreased and at 50 ug most of the PR sedimented in the 4S region. Experiments in which PR was first incubated with 50 ug of the oligopeptide and then reincubated with the monoclonal antibody produced similar results to those shown in FIG. 5D. Incubation of PR with the free peptide in absence of the antibody and subsequent analysis on SDG did not alter the sedimentation of the PR complex. Furthermore, incubation of the antibody with synthetic peptides derived from human estrogen receptor sequences also did not influence antibody-PR interaction. These observations clearly indicate that the monoclonal antibody (PR-AT 4.14) is site specific with respect to the epitope spanning amino acids 533–547 of human PR.

Other PR Binding Properties

Figure 6C:
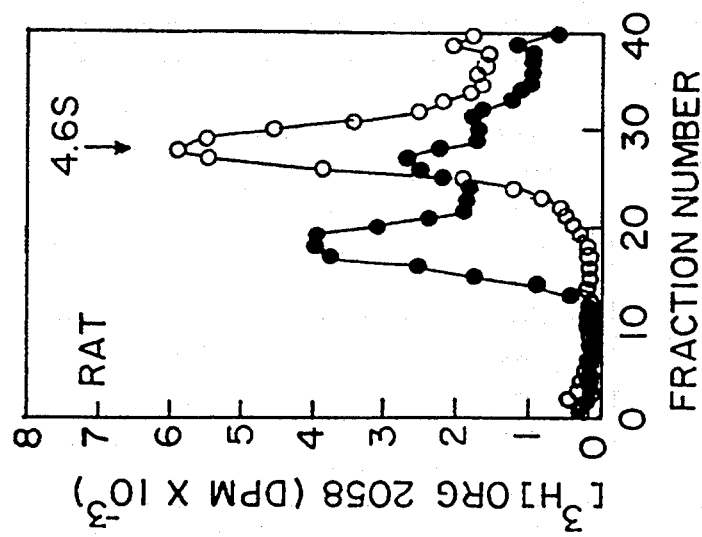
FIGS. 6A-6C are graphs illustrating the interaction of the monoclonal antibody with progesterone receptor from non-human sources.
Figure 6B:
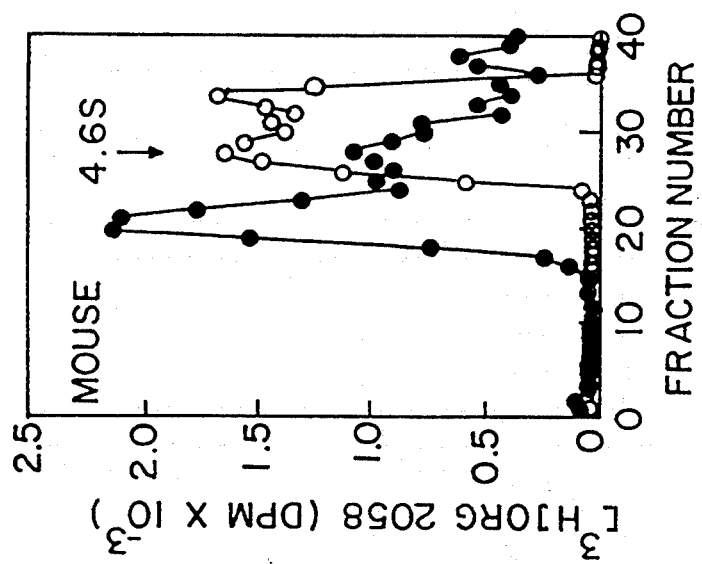
Figure 6A:
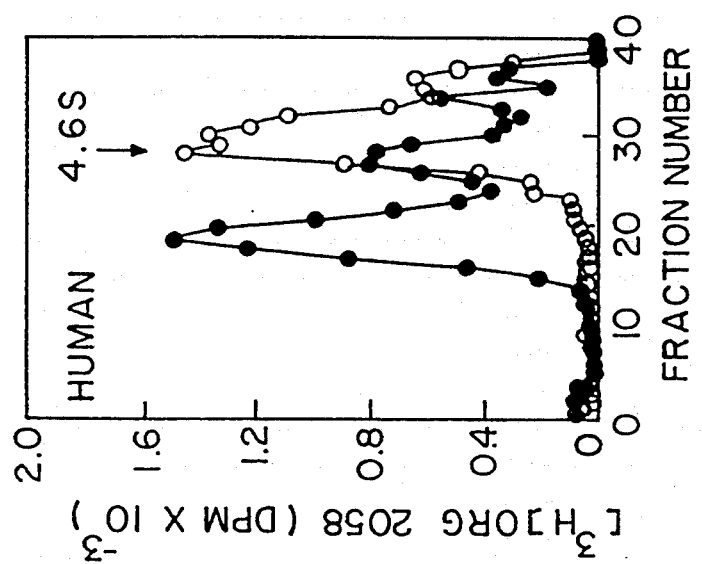

The progesterone family is characterized by the presence of two conserved regions: namely, the DNA-binding and the steroid binding domains. Since these monoclonal antibodies are produced specifically against an epitope adjacent to the DNA-binding domain, it is possible that such antibody may recognize PR from other, non-human species. It is also possible that this domain is in the hypervariable region and that differences in the amino acid sequences in this region may exist. This could result in lack of recognition of PR from other species by such antibody. To test this, PR from uterine tissues of several species was incubated with PR-AT 4.14 antibody and then analyzed on SDG in the presence of KCl. FIG. 6 shows that the monoclonal antibody recognized PR from human (panel A), mouse (panel B), and rat (panel C); while FIG. 2 shows recognition of calf PR as indicated by the increased sedimentation rate of PR. These comparative results indicate that this domain is probably similar, if not identical among these species. Further experiments showed that this monoclonal antibody also cross-reacted with rabbit uterine PR (data not shown). Comparison of the protein primary sequence showed that hPR and rabbit PR had similar amino acid sequences in this region with only one amino acid substitution from Thr to Pro [Loosfelt et al., *Proc. Natl. Acad. Sci. USA* 83:9045–9049 (1986)]. Thus, it is not surprising that the one monoclonal antibody cross-reacted with PR from among the species tested.

Ability to Bind To Other Steroid/Receptors

The antibody specificity with respect to estrogen receptor ("ER"), glucocorticoid receptor ("GR"), and androgen receptor ("AR") was then evaluated. To label steroid receptors, the cytosols were incubated at 0° C. for 16 h with the appropriate ligands. Progesterone receptors from various tissue cytosols were labeled with 10 nM [$^3$H]-ORG 2058 in the absence (total binding) or the presence (nonspecific binding) of a 100-fold molar excess of unlabelled ORG 2058 as described by Traish et al. [*Steroids* 47:157r173 (1986)]. Estrogen receptors from calf uterine cytosol were labelled with 5 nM [$^3$H]-estradiol in the absence of the presence of unlabelled estradiol as described by Muller et al. [*J. Biol. Chem.* 258:9227–9236 (1983)]. Androgen receptors were labelled by incubating rat prostate cytosol with 10 nM [$^3$H]-mibolerone in the absence or presence of unlabelled mibolerone as described by Traish et al. [*Endocrinology* 118:1327–1333 (1986)]. Similarly, glucocorticoid receptors were labelled by incubating calf uterine cytosol with 10 nM [$^3$H]-dexamethasone in the absence or presence of unlabelled dexamethasone as described. At the end of the incubation, unbound radioactive steroids were removed with dextran coated charcoal pellets and the supernatants were used for antibody receptor interaction.

Figure 7A:
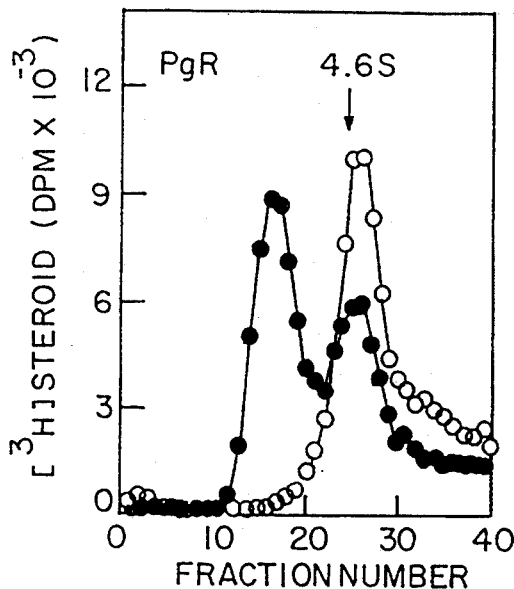
FIGS. 7A-7D are graphs illustrating the receptor-specificity of the monoclonal antibody.
Figure 7B:
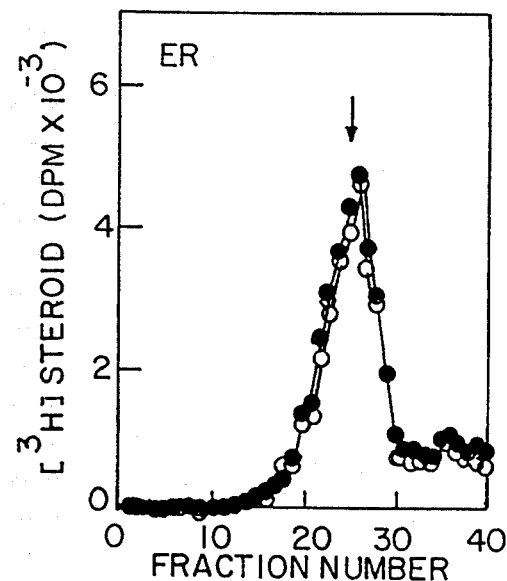
Figure 7C:
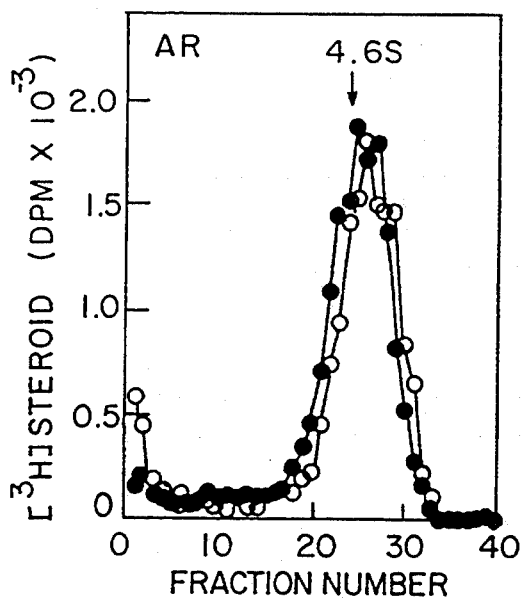
Figure 7D:
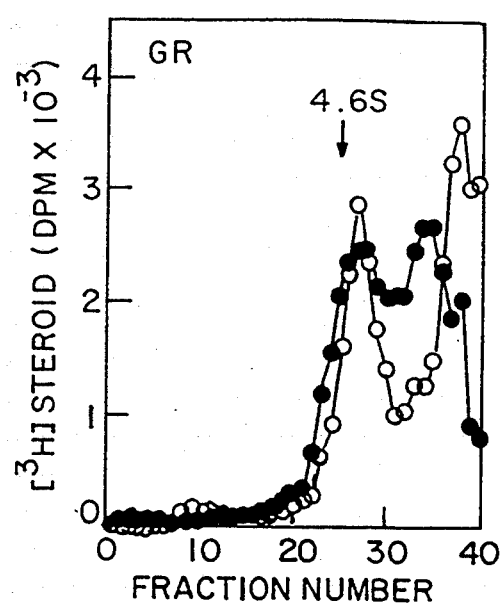

Accordingly, aliquots of cytosols containing labelled ER, AR, or GR were incubated with the antibody and then analyzed on SDG containing KCl. The results in FIG. 7 clearly show that the monoclonal antibody was specific to PR (FIG. 7A) since it reacted with PR, but did not cross-react with estrogen receptor (FIG. 7B), androgen receptor (FIG. 7C), or glucocorticoid receptor (FIG. 7D), as indicated by the lack of increase in the sedimentation rate of these receptors in the presence of the antibody.

When human PR from 18 breast cancer specimens was analyzed using this epitope-specific monoclonal antibody, it was found that two populations of PR existed. One population of PR bound the antibody and sedimented as an 8S complex in the presence of 0.4M KCl while a second population sedimented at 4S regardless of the presence or absence of the antibody. The distribution of the antibody-bound PR and the unbound PR was different among the tumors. This observation could be attributed to either presence of two receptor species (namely A and B), insufficient concentrations of antibody used in the incubation, or proteolysis of PR at or near the antibody binding-site during cytosol preparation and/or labelling incubation.

Figure 8A:
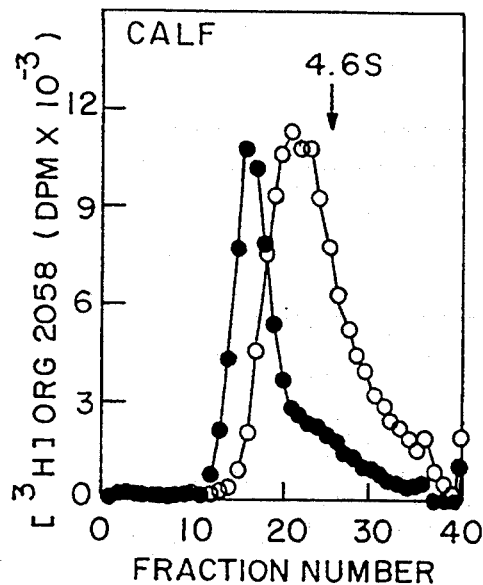
FIGS. 8A-8D are graphs illustrating the binding of the monoclonal antibody to PR in the presence and absence of proteolysis inhibitors and molybdate.
Figure 8B:
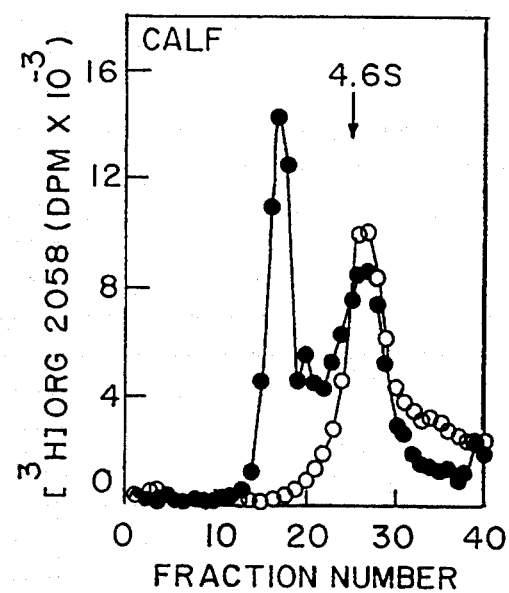
Figure 8C:
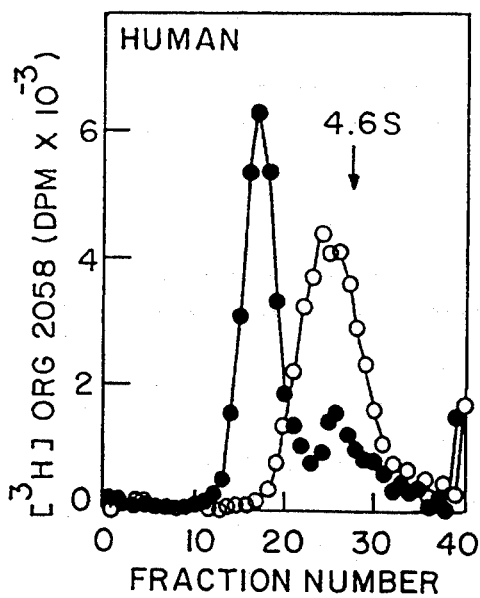
Figure 8D:
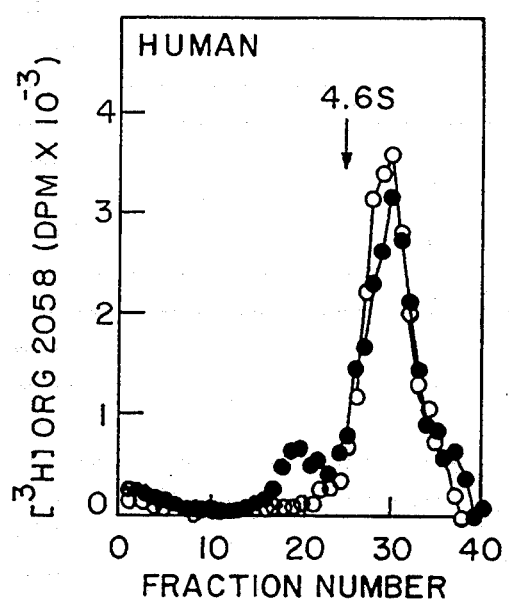

To test these possibilities, experiments were performed in which cytosols from calf uterine and human breast tissues were prepared either in the absence or presence of the following proteolysis inhibitors: 0.5 mM PMSF, 1 ug/ml leupeptin, 10 ug/ml bacitracin, 20 KI-U/ml aprotonin, 10 ug/ml pepstatin, and 10 mM sodium molybdate. The results are shown by FIG. 8. The data show that calf uterine PR prepared and labelled in the presence of molybdate and proteolysis inhibitors bound to the antibody and sedimented as one population (FIG. 8A, solid circles). In contrast, when the receptor was prepared and labelled in the absence of molybdate and proteolysis inhibitors and then incubated with the antibody (FIG. 8B), two populations of PR appeared—suggesting that proteolysis may have contributed to the inability of the antibody to bind the partially degraded receptor. When human breast cancer PR complexes were prepared and labelled in the presence of molybdate and proteolysis inhibitors and then incubated with the antibody, the majority of PR complexes sedimented in the 8S region (FIG. 8C). Incubation of PR with the antibody in the absence of molybdate and proteolysis inhibitors and subsequent analysis on sucrose density gradients demonstrated the inability of the epitope-specific monoclonal antibody to bind to proteolyzed receptors (FIG. 8D). These data reveal that the antibody recognized only the intact PR complexes.

To rule out the possibility that the concentrations of the monoclonal antibody used in these experiments were insufficient and, therefore, would not bind all the available PR, a wide range of antibody concentrations (0.1–50 ug) were used. PR complexes were prepared and labelled in the presence of molybdate and proteolysis inhibitors as described above. Subsequent incubation with increasing concentrations of antibody and analysis on sucrose density gradients were made with or without KCl. The results are given with FIG. 9. As shown therein, at each antibody concentration, both the untransformed 8S (open circles) and the salt transformed 4S (solid circles) PR complexes sedimented at greater rate than the control (FIG. 9A). All the labelled PR complexes sedimented as large molecular weight complexes in the presence of the epitope-specific monoclonal antibody, suggesting that the antibody concentrations used in previous experiments were sufficient to complex all of the available PR. These data further indicate that the monoclonal antibody binds to the intact receptor; and that proteolysis at or near the antibody binding site renders the receptor incapable of binding to the antibody. The possibility that the antibody recognized only one of the receptor subtypes is unlikely since in the presence of proteolysis inhibitors all labelled PR bound to the antibody.

To demonstrate that the binding data obtained with this monoclonal antibody is specific to PR, we have used monoclonal antibodies produced against the human ER (estrogen receptor) to determine the antibody-binding specificity. It was previously shown that PR did not bind to monoclonal antibodies prepared against small peptides from hER. These results suggested that the monoclonal antibody (PR-AT 4.14) produced against a single oligopeptide is specific to a unique epitope of the human PR. Analysis of PR by western blot technique using this antibody did not demonstrate binding of this antibody to PR subsequent to denaturation by SDS-PAGE, revealing that the monoclonal antibody did not recognize the denatured receptor (data not shown). Preincubation of PR preparations with monoclonal antibody did not inhibit binding of transformed PR to DNA-cellulose (data not shown), suggesting that the antibody bound to a region distal to the DNA-binding domain. This is not surprising since the antibody binding-site is available in the molybdate stabilized untransformed (8S) and the salt transformed (4S) PR complexes.

Overall Summary

Monoclonal antibody specific for a single epitope of human PR was characterized with respect to site-specificity, receptor-specificity, and cross-reactivity with PR from other species. The monoclonal antibody bound specifically and with high affinity to PR as demonstrated by sucrose density gradient analysis and immunoprecipitation assays. The ability of the free oligopeptide comprising amino acid Nos. 533–547 of hPR to compete for receptor binding to the antibody and the inability of other unrelated peptides derived from the hER to compete for PR binding indicates that the antibody is site specific. The antibody did not bind to ER, AR, and GR suggesting that this epitope is not shared by these receptor proteins. The antibody, however, bound to PR from human breast cancer rat, mouse, rabbit, and calf uterine tissues, suggesting that this domain is either identical or similar in PR from these species. Thus, although the oligopeptide used as an immunogen is in the hypervariable, N-terminal region there appears significant homology in the receptor among these species.

The present invention is not to be restricted in form nor limited in scope except by the claims appended hereto.

What we claim is:

1. An in-vitro method for ascertaining the functional integrity of human progesterone receptor protein in a cellular sample, said method comprising the steps of:
providing at least one monoclonal antibody specific for a single epitope in the native (8S) and transformed (4S) forms of human progesterone receptor protein, said epitope located within amino acid residues 533–547 of human progesterone receptor protein;

mixing said monoclonal antibody with a cellular sample whereby said monoclonal antibody binds specifically to such 8S and 4S forms of human progesterone receptor protein as are present in said cellular sample; and determining the presence of bound monoclonal antibody within said cellular sample, the presence of said bound monoclonal antibody serving as a measure for ascertaining the functional integrity of the human progesterone receptor protein within the cellular sample.

2. The in-vitro method as recited in claim 1 wherein said monoclonal antibody comprises an identifying label.

3. The in-vitro method as recited in claim 2 wherein said identifying label is selected from the group consisting of isotopic and non-isotopic labels.

4. A test kit for ascertaining the functional integrity of human progesterone receptor protein using an in-vitro methodology, said test kit comprising:

at least one container of a monoclonal antibody specific for a single epitope in the native (8S) and transformed (4S) forms of human progesterone receptor, said epitope located within amino acid residues 533–547 of human progesterone receptor protein;

at least one container of a liquid buffer of defined formulation for mixing with said monoclonal antibody; and at least one container containing a known quantity of progesterone receptor protein in at least one form selected from the group consisting of the native (8S) and transformed (4S) forms of progesterone receptor protein.

* * * * *